United States Patent [19]

Cruz, Jr.

[11] 4,148,664
[45] Apr. 10, 1979

[54] PREPARATION OF FIBROUS COLLAGEN PRODUCT HAVING HEMOSTATIC AND WOUND SEALING PROPERTIES

[75] Inventor: Mamerto M. Cruz, Jr., Pennington, N.J.

[73] Assignee: Avicon, Inc., Fort Worth, Tex.

[21] Appl. No.: 897,502

[22] Filed: Apr. 18, 1978

Related U.S. Application Data

[60] Continuation of Ser. No. 684,940, May 10, 1976, abandoned, which is a continuation-in-part of Ser. No. 466,214, May 2, 1974, abandoned, which is a continuation of Ser. No. 358,145, May 7, 1973, abandoned, which is a division of Ser. No. 76,638, Sep. 29, 1970, Pat. No. 3,742,955.

[51] Int. Cl.² ..................... C08L 89/00; C09H 1/00
[52] U.S. Cl. .................................................. 106/161
[58] Field of Search ..................................... 106/161

[56] References Cited

U.S. PATENT DOCUMENTS

| 2,928,822 | 3/1960 | Johnson et al. | 260/117 |
| 3,628,974 | 12/1971 | Battista | 106/125 |

Primary Examiner—Theodore Morris
Attorney, Agent, or Firm—George F. Mueller; Robert D. Jackson

[57] ABSTRACT

A fluffy, finely-divided fibrous collagen derived product having hemostatic and adhesive properties sufficient to join together severed biological surfaces in a live warm blooded animal when the product is wet with blood between the surfaces. In the preparation of the product, water-wet collagen is treated with ethanol to remove water, is converted to a ionizable partial salt in the presence of ethanol and dehydrated with ethanol so as to control and limit the swelling of the collagen fibers and prevent hornification upon drying. The recovered dry material is subjected to deaggregation to form a mass having a bulk density of not more than 8 pounds per cubic foot and a surface area of at least 1 square meter per gram.

4 Claims, No Drawings

PREPARATION OF FIBROUS COLLAGEN PRODUCT HAVING HEMOSTATIC AND WOUND SEALING PROPERTIES

This application is a continuation of application Ser. No. 684,940 filed May 10, 1976, which is a continuation-in-part of application Ser. No. 466,214, filed May 2, 1974, which is a continuation of application Ser. No. 358,145, filed May 7, 1973 all abandoned, which is a division of application Ser. No. 76,638, filed Sept. 29, 1970, now U.S. Pat. No. 3,742,955 granted July 3, 1973.

This invention relates to a specific form of finely-divided fibrous collagen and fibrous products derived from collagen particularly adapted for use in medical and surgical procedures.

Collagen in various treated or prepared forms is useful in surgery and the treatment of wounds as shown for example, in U.S. Pat. No. 3,157,524 to C. Artandi and J. F. Prudden, Arch. Surg. 89, 1046–1059, December 1964. E. E. Peacock, Jr. et al, Ann. Surg. 161, 238–247, February 1965, among others teach that collagen has hemostatic properties when used as a wound dressing, and has a low level of antigenicity. It has now been found that fibrous collagen and fibrous products derived from collagen, when properly prepared and when wet with blood, will not only demonstrate hemostasis but also demonstrates an unexpected adhesiveness to severed biological surfaces in warm blooded animals. Thus, this new form of collagen, unlike other forms of collagen suitable for use in the treatment of wounds, demonstrates an unexpected and unique adhesiveness between two severed biological surfaces and in many instances can actually be used to adhere severed tissue without the use of sutures as well as to effect hemostasis.

It is a primary object of this invention to provide a finely-divided fibrous collagen and fibrous products derived from collagen which are useful in effecting hemostasis of and adhesiveness between two severed biological surfaces in warm blooded animals.

It is another object of this invention to provide a method of preparing a finely-divided fibrous collagen and fibrous products derived from collagen which are useful hemostatic agents and have unique adhesive properties in contact with a severed biological surface in a warm blooded animal when wet with blood.

These and other objects are attained in accordance with this invention with a composition of matter comprising finely-divided fibrous collagen products having a surface area of at least 1 square meter per gram, preferably from about 15 to about 30 square meters per gram, and a bulk density of not more than about 8 pounds per cubic foot, preferably between about 1.5 and 6.0 pounds per cubic foot. The preferred fibrous collagen products are partial, ionizable acid salts of collagen containing from about 50% to 90% of the theoretical stoichiometric bound acid content.

The surface area is determined by the conventional nitrogen adsorption method using the Perkin-Elmer Sorptometer. The bulk density is determined by adding the fibrous product to a container of known volume without compression and weighing the amount of added material.

The fibrous collagen products having the foregoing characteristics possess unique adhesive properties when wet with blood and these adhesive characteristics are demonstratable in surgical experiments with animals. Fibrous collagen products outside the scope of the products of the present invention do not exhibit the unique adhesive properties. As will be described herinafter, an in vitro procedure has been devised for measuring the adhesive properties of the fibrous collagen products when wet with blood.

The fibrous collagen products may be prepared by mechanically dicing or chopping wet, undenatured collagen or delimed edible collagen, fiberizing the diced or chopped collagen, mechanically dispersing the collagen fibers in an aqueous liquid which controls the swelling of the collagen fibers, replacing the bulk of the water associated with the fibers by a water-miscible organic liquid, drying the fibrous collagen product and finally deaggregating the collagen fibrils or fluffing the dried product. Alternatively, the wet undenatured collagen or delimed collagen is mechanically diced or chopped, treated with a water-miscible organic liquid to remove the bulk of the water, dried and then subjected to the final deaggregating or fluffing operation.

The wet collagen such as hide is diced or chopped into small fragments of from $\frac{1}{4}$ to $\frac{1}{2}$ inch sizes in a cutting or grinding mill, such as, for example, an Urschel Mill. These fragments may be mixed with crushed ice and then passed through the Urschel Mill with cutting heads of smaller dimension to fiberize the collagen into a coarse fibrous product.

If swelling or hydration of the collagen fibers is not controlled during the subsequent treatment wherein the collagen is subjected to mechanical shredding or opening in a liquid medium excessive hydrogen bonding or densification will occur when the material is dried down thereby effectively preventing the satisfactory deaggregation of the collagen fibrils during the final mechanical treatment. The initial swelling of the collagen fibers in the wet state affords many more sites for hydrogen bonding than is desirable thus leading to a dried material which may be hornified and difficult to deaggregate into the constituent fibrils or "fluff". When hornification and densification occurs, the product will not have the required physical characteristics so as to provide the desired adhesion to severed biological surfaces in warm blooded animals when wet with blood nor will it provide the required mechanical properties of the collagen-blood matrix between the severed surfaces.

The terminology "mechanical properties of the collagen-blood matrix" is used to designate the property of a mixture of the fibrous collagen product and blood which holds together the mixture sufficiently and has sufficient tensile strength to resist separation of the fibers and thereby seal the wound. The in vitro test procedure to be described is a direct measure of this mechanical property.

The wet or moist fibrous collagen is mechanically opened and the fibers dispersed in an aqueous liquid which controls the swelling of the fibers. The aqueous liquid comprises water and a water-miscible organic liquid such as low molecular weight alcohols, acetone, and the like. The liquid may comprise the organic liquid such as methanol, ethanol, isopropanol, methylethyl ketone, acetone and the like and water in a weight range of from about 90% of the organic liquid to 10% water to about 50% organic liquid to 50% water, preferably 75% organic liquid and 25% water. Where the proportion of water is too high, the collagen fibers swell to such a great extent that a larger number of sites are provided for hydrogen bonding and attendant densification during the subsequent drying step. When this occurs, excessive hornification and/or densification occurs and it becomes commercially unfeasible to subsequently deaggregate or fluff the fibrous product and attain the bulk density and the surface area requirements necessary for the present invention. Although such product will possess some hemostatic properties, it does not possess the desired adhesion to severed biological surfaces and will not provide the required mechanical properties of the collagen-blood matrix between the severed surfaces.

The bulk of the liquid is drained from the mass and the fibrous collagen slurried and washed with a water-miscible organic liquid such as the alcohol or acetone and again the bulk of the liquid is separated from the partially swollen wet fibers. Preferably, the fibrous material is slurried in the organic liquid to reduce the water content to a minimum. In general, the use of three slurrying steps with the organic liquid will reduce the amount of water present to above 1%. The organic liquid is removed as by centrifugation and final drying. Drying may be effected either by oven drying or vacuum drying as at, for example, 40° C. under a 29 inch vacuum for about 16 hours. In general, this vacuum drying will reduce the volatile content to under 1%.

Before the final deaggregation into constituent fibers or fluffing operation to produce the product having the required surface area and bulk density, the fibrous material is preferably conditioned to contain about 8% to 15% volatiles such as water and/or organic liquid. This conditioning may be readily effected by allowing the product to remain at normal atmospheric temperatures and humidities for from about 8 to 24 hours. The final fiber deaggregation or fluffing operation is necessary to provide the requisite bulk density and surface area. This operation is, in effect, an "opening" operation which is somewhat comparable to the deaggregation of chrysotile fibrils. In this art, this opening separates some fiber bundles into their ultimate individual chrysotile fibrils. In forming the product of the present invention, the final fiber deaggregation or fluffing operation does not separate all of the dried bundles into ultimate individual fibrils but the product does contain finer fiber bundles (smaller in diameter) as compared to the coarser fiber bundles obtained at the end of the drying and conditioning operations. This deaggregation or fluffing may be effected by apparatus such as a Waring Blendor or, preferably, a hammer mill type comminution mill such as a Fitz Mill.

Where it is desired to produce a partial salt of collagen, the required amount of an ionizable acid may be incorporated in the aqueous liquid wherein the fibrous collagen is dispersed. The amount of acid incorporated in the aqueous liquid is such as to provide the product with a bound acid content of from about 50% to 90% preferably about 60% of the theoretical stoichiometric bound acid content. After the acid has reacted with the dispersed collagen, the reaction mass is subjected to slurrying and washing with the water-miscible organic liquid and the collagen salt processed as above described.

Alternatively, the partial ionizable salt of collagen may be prepared as described in the copending application of Orlando A. Battista, Ser. No. 14,709, filed Feb. 9, 1970. In accordance with the method described in that application, diced or chopped undenatured collagen is introduced into and mixed in a water solution of an ionizable acid, the pH of the solution being between about 1.6 and about 2.6 based upon a 1% by weight solids content of the mixture. The mixture is agitated to permit the desired reaction between the collagen and acid and produce a partial salt of collagen containing between about 50% and 90% of the theoretical stoichiometric bound acid content.

After separating the reacted collagen from the bulk of the solution and washing it, the fibrous product may be recovered by drying. Because of the use of the aqueous liquids, hydrogen bonding occurs and the product is hornified to some extent. A product satisfactory for the present invention may be obtained by a severe deaggregation procedure and fluffing operation. For example, a fibrous product prepared in this manner will require a minimum of two passes through a hammer mill such as a Fitz Mill in order to provide the requisite bulk density and surface area.

Although the partial salt of collagen may be prepared by the use of the water-acid solution in a manner as described, the partial salt after its formation and recovery in a wet state may be slurried and washed several times with a water-miscible organic liquid as described above and then dried. Such product will be less hornified than that dried directly from the water system. In general, such product requires only two passes through a Fitz Mill to produce a final product having the required bulk density and surface area.

Alternatively, the wet collagen source material is diced or chopped into small fragments and then introduced into and mixed in a water-miscible organic liquid such as ethanol or isopropanol. Mixing is continued for about one hour so as to permit thorough penetration of the organic liquid into the small fragments. The bulk of the liquid is then separated as by draining or centrifuging and the recovered fragments again introduced into and mixed in the organic liquid for about one hour. Again, the bulk of the liquid is separated and the procedure repeated. At the end of this period, the liquid is centrifuged from the mixture and the wet fragments dried as by oven drying or vacuum drying. The resulting product, after conditioning as described above, is then subjected to a fiberizing and deaggregation or fluffing operation. If it is desired to produce a partial ionizable salt of collagen, the desired amount of acid may be mixed with the organic liquid in any one of the above described steps. In such instances, the time of treatment with the organic liquid containing the acid should be prolonged to permit the required reaction between the acid and the collagen. Obviously, the time periods may be reduced by operating under pressure.

The foregoing discussion describes, in general, the preparation of products under conditions wherein the pH of the treating solution is neutral or below pH 7. Products having the required bulk density, surface area and adhesive characteristics may also be prepared wherein the treating solution is on the alkaline side; that is, at a pH above 7. Thus, products with the required properties have been prepared by substituting an alkali such as sodium hydroxide, potassium hydroxide and ammonium hydroxide for the acid of the treating solutions. These treating solutions had a pH of approximately 9. The processing procedures are identical to those described hereinabove.

The suitability of the collagen product for its intended uses may be determined by a relatively simple laboratory in vitro procedure which has been termed a "HAT Test" or "Hemostat-Adhesive Test". In this procedure, a cone penetration test is performed utilizing a Penetrometer such as used the testing of lubricating greases and bituminous materials in accordance with ASTM D 217-67 T. In this test, 1.2 grams of the fibrous collagen product is mixed with 3.5 mls. of outdated human blood, that is, between 21 and 31 days after it was drawn and stabilized with standard citrate solutions in accordance with normal procedures.

The blood is transferred to a cavity (0.753" diam., 0.875" deep) in a plastic block, and the fibrous product slowly added and uniformly mixed with the blood. It is important that all of the fibers are wetted by the blood and that the mass is of homogeneous structure. The surface of the mass is made smooth. Mixing and smoothening are conveniently accomplished by use of a narrow stainless steel spatula.

The block is inserted loosely in a polyethylene bag, placed in an oven maintained at approximately 98° F. and held in the oven for 60 minutes 35 one minute. At the end of this period, the block is removed and placed on the Penetrometer stage.

The head of the mechanism as used in this procedure consists only of the stainless steel nipple at the end of the normal penetrometer cone. It is adjusted so as to bring the point of the penetrating cone exactly into contact with the surface of the sample. The rod supporting the penetrating cone is then released to allow the cone to penetrate the sample for a period of 5 seconds at the end of which the supporting rod and cone are locked into position. A gauge is actuated to measure the change in position of the rod which is equivalent to the penetration of the cone into the sample. The standard Penetrometer gauge measures this distance in tenths of a millimeter. In the testing of the samples, three penetration tests are applied to each sample at different positions on the surface of the sample. The results, the average of the three penetration tests, are expressed as distance in tenths of a millimeter × 10 and reported as "HAT Rating". It is obvious that the greater the adhesion between the blood wetted fibers the greater the tensile strength of the mass and, accordingly, the amount of the penetration of the cone into the mass is inversely proportional to the strength of the mass.

If nubs or gritty particles and/or blobs of fibers are evident during the initial mixing of the sample and the blood, but no unabsorbed blood is evident in the cavity, the test is run in the normal manner. However, such samples should be removed from the cavity at the completion of the Penetrometer reading, and the plug examined with a spatula to determine if any of the more dense particles have not been completely soaked through by the blood. If there appear nubs or particles with cores that are white indicating nonuniform wetting the blood, the test data is invalidated and the sample rerun using more thorough blending during the initial mixing step.

In addition, the sample is considered to have failed this test if after the initial mixing unabsorbed blood appears freely in the cavity.

While a wide variety of materials exhibit various degrees of hemostatic properties, it is only a relatively narrow range of the collagen products of this invention which, in addition to having the hemostatic properties, also have an adhesive property rendering them satisfactory in adhering severed tissues. It has been found that there is a direct correlation between the HAT Test and the in vivo tests in animals involving veins, the spleen and the liver. In general, the products found to be satisfactory as both a hemostat and an adhesive exhibit HAT Tests, or HAT Ratings, not exceedng about 1500, preferably below 900. It has also been observed that, in general, samples of products which possess the combined hemostatic and adhesive characteristics when mixed with human blood an incubated for one hour at 98° F. exhibit a dark red to black color whereas those products which lack the adhesive properties exhibit a red to bright red color.

It has also been discovered that in order for the product to exhibit the desired properties it is preferable that it contain at least about 5% by weight of fibers having an effective length of not more than 1 mm. and not over 10% have a length above mm. Where the proportion of short fibers (not more than 1 mm.) is below the lower limit, there appears to be a clumping or aggregation of longer fibers with a loss in both hemostatic and adhesive properties. Where the proportion of short fibers is too high, there is a loss in adhesive properties. One measure of the fiber length distribution and the fluffiness of the products is bulk density and the bulk density of the products satisfactory for the present purposes is not more than 8 pounds per cubic foot. The bulk density is measured by adding the fibrous collagen products as initially fluffed to a 100 ml. graduate cylinder without any compression step and determining the weight of the added 100 mls of the product.

The finely-divided fibrous collagen product of this invention can be prepared from an undenatured collagen in the natural state or delimed edible forms of collagen including, for example, hide, gut, tendon, cartilage or other high fibrous collagen source material preferably chopped up for easier handling. The collagen is preferably in a wet and never-dried state or, if dried, drying has been effected under conditions which minimize denaturization. Satisfactory raw materials for the collagen include, for example, fresh cowhides and calfhides, salted down cowhides, wet moosehide, pigskins, sheepskins and goatskin as conventionally used for making leather. Special technical hide collagen prepared from hide splits and possessing a minimal reduced bacteria count is also satisfactory. The preferred raw material, because of availability is never-dried cowhide or technical grades of collagen prepared from cowhide and other animal hides.

In forming the partial salt of collagen, hydrochloric acid is the referred acid and is used in the examples which flow merely because it is relatively inexpensive and allows ready flexibility and ease of control. Other ionizable acids, both inorganic and ionizable organic acids, such as, for example, sulfuric acid, hydrobromic acid, phosphoric acid, cyanoacetic acid, acetic acid, citric acid and lactic acid are satisfactory. Sulfuric acid, for example, is satisfactory, but control of the action is difficult. Citric acid may be substituted for hydrochloric acid with about equal results. "Ease of control" has reference to the ability to arrest the swelling and hydrolysis of the collagen fibers so as to prevent the rapid degradation of the material to a water-soluble product.

In the examples which flow, Examples I and II describe the preparation of a preferred partial salt of collagen and reference will be made to the product of Example II as a standard for purposes of comparison. In addition to measuring the bulk density and surface area, a suspension (1/2% by weight) of each sample was subjected to the action of a Waring Blendor at high speed for 30 minutes and the pH of the suspension was then measured. The properties of the fluffy finely-divided fibrous products of the examples were as reported in Table I.

EXAMPLE I

Raw or green bovine corium was cut into 3 inch strips, the lengths varied depending upon the position in the original hide, and were then frozen for future processing. A desired number of strips were subsequently allowed to thaw for about 1 day and washed several times with water at a temperature of about 10° C.-11° C. After the excess water had been allowed to drain, the wet strips were diced into chips or pieces of ¼" to ½" size. Specifically, the dicing was accomplished by feeding manually the strips into an Urschel MIll (Comitrol Model 1300) having a circular cutting head fitted with bars having a width of 0.030" spaced apart 0.510". The revolving impeller had a clearance of 0.007" from the cutting head and was operated at 4140 rpm. The diced material was mixed with crushed ice and passed through the Urschel Mill fitted with bars having a width of 0.010" spaced apart 0.040" to fiberize the collagen. The temperature during dicing and fiberizing was between 10° C. and about 15°C. and the solids content of the fiberized mass was about 25%. The mass was then centrifuged to a solids content of approximately 30%.

A mixture was prepared containing about 108 pounds of isopropanol and 373 mls. of 12N HCl. To this mixture was added 51.5 pounds of the fiberized mass. Since the fiberized mass contained about 36 pounds of water, the aqueous liquid contained approximately 75% isopropanol and 25% water. The amount of hydrogen chloride was approximately 90% of the theoretical stoichiometric amount of acid required to react with all amino groups of the collagen. The solids content (collagen) was about 9.7%. The slurry was mixed in a Lightnin mixer operating at 115 rpm. for 3 hours and then centrifuged to a solids content of about 40%, 39 pounds of cake resulting.

The cake was then introduced into about 115 pounds of isopropanol (containing about 1.5 pounds of water) in a Lightnin mixer and the fibers slurried for 2 hours. The mass was centrifuged to reduce the cake to a solids content of about 40%. The cake was reslurried in 117 pounds of isopropanol (containing about 1.1 pounds of water) and again centrifuged. All of the liquid treatments were carried out at temperatures between about 25° C. and 28° C.

The cake was vacuum dried under 28"-29.5" of mercury at 60° C. for about 22 hours and resulted in the recovery of 15.25 pounds of fibrous collagen product. The fibrous product was then conditioned by exposure to the room atmosphere over a weekend and contained about 11% moisture.

The resulting fibrous mass was then subjected to a deaggregating or fluffing operation by passing through a hammer mill and screening. Specifically, the mass was passed through a Fitz Mill (Model DA50-6-5634) operated at 6250 rpm. and equipped with a #4 screen having openings of 0.243".

The final fluffed product contained 0.658 meq. HCl per gram of collagen (approximately 84% of the theoretical stoichiometric amount). The bulk density was 2.5 pounds per cubic foot and the surface area of various samples varied from 18.1 to 23.0 square meters per gram. The HAT Rating was 799 with AB+ blood and 850 using A+ blood. Upon disintegrating a sample of the product in water by subjecting a suspension containing 0.52% by weight of the fluffy, finely-divided fibers in water to the action of a Waring Blendor for 30 minutes, a stable dispersion was formed having a pH of 3.30.

EXAMPLE II

The product used as a standard for the in vivo tests was obtained by subjecting the product of Example I to screening in a Rotap for 1 hour and using the material retained on a #14 Sieve. The bulk density was 2.5 pounds per cubic foot, the surface area was 24 square meters per gram and the HAT Rating was 700 with A-blood.

EXAMPLE III

Example I was repeated but ethyl alcohol was substituted for the isopropanol of Example I.

EXAMPLE IV

Example I was repeated but methyl ethyl ketone was substituted for the isopropanol of Example I. The dried conditioned product was deaggregated or fluffed dry in a Waring Blendor for 1 minute at high speed.

EXAMPLE V

Example I was repeated substituting delimed split corium for the raw corium of Example I.

EXAMPLE VI

Example III was repeated but no acid was added to the ethanol-water treating solution. The deaggregated, fluffy product was subsequently screened through a No. 4 screen, followed by a pass through an 18 mesh screen (0.039" openings).

EXAMPLE VII

Example III was repeated but no acid was added to the ethanol-water treating solution and the final deaggregation and fluffing treatment was altered. The conditioned fibrous mass was first passed through a Fitz Mill provided with a No 2A screen closed by a polyester film on the back side of the screen followed by a second pass using a No. 2AA screen having 0.079" openings.

EXAMPLE VIII

Example I was repeated using freeze-dried, green corium in place of the raw corium, omitting the acid and adjusting the pH of the liquor to pH 9 by addition of 0.01N NaOH solution. The dried conditioned product was deaggregated or fluffed dry in a Waring Blendor for 1 minute at high speed.

EXAMPLE IX

Example I was repeated using freeze-dried, green corium in place of the raw corium, omitting the acid and adjusting the pH to 8.0 using 0.05N ammonium hydroxide.

EXAMPLE X

Strips of wet green corium (about 30% collagen) were diced into chips or pieces ¼" to ½" in size. A mixture was prepared containing about 108 pounds of ethyl alcohol (200 proof) and 51.5 pounds of the wet diced corium. The solids content (collagen) was about 9.7%. The mixture was agitated in a Lightnin mixer operating at 115 rpm for 1 hour and then centrifuged to a solids content of about 40%.

The cake was then added to a mixture of about 115 pounds of ethyl alcohol and 373 mls. of 12N HCl and the mixture agitated in a Lightnin mixer for about 20 hours. The mass was then centrifuged to reduce the cake to a solids content of about 40%. The cake was reslurried in 117 pounds of ethyl alcohol and again centrifuged. All of the liquid treatments were carried out at temperatures between about 25° C. and 28° C.

The cake was vacuum dried under 28"–29.5" of mercury at 60° C. for about 22 hours and resulted in the recovery of 15.25 pounds of the collagen product. The callagen product was then conditioned by exposure to the room atmosphere for about 24 hours and contained about 11% moisture.

The resulting conditioned mass was then subjected to a deaggregating or fluffing operation by passing through a hammer mill and screening. Specifically, the mass was passed through a Fitz Mill (Model DA50-6-5634) operated at 6250 rpm. and equipped with a #4 screen having openings of 0.243". It was then subjected to a second pass using No. 2A screen (0.064").

The final fluffed product contained 0.65 meq. HCl per gram of collagen (approximately 84% of the theoretical stoichiometric amount). The bulk density was 1.5 pounds per cubic foot and the surface area was approximately 1.9 square meters per gram. The HAT Rating was 483 with AB+ blood and 477 using A-blood Upon disintegrating a sample of the product in water by subjecting a suspension containing about 0.5% by weight of the fluffy, finely-divided fibers in water to the act of a Waring Blendor at high speed for 30 minutes, a stable dispersion was formed having a pH of 3.10.

The fibrous collagen products prepared in the above examples were employed in surgical test procedures designed to prove the efficacy of the material both as a hemostat and adhesive for severed biological surfaces in a warm blooded animal when wet with blood. "Severed" biological surfaces for the purposes of this invention includes cut, sliced, ripped, abraded, torn, punctured, burned, and tissue severed by any means or method whereby a fresh biological surface is present. Biological surfaces will include tissue, cartilage, vesels, bone or other normal organic parts of the warm blooded animal which may require mending or joining.

The in vivo surgical test procedure in one series of experiments was carried out on mongrel dogs and involved the makng of a two inch capsule-to-capsule laceration in the leading edge of the liver and spleen. The actively bleeding lacerations were packed with as much of the fibrous collagen product as necessary to effect hemostasis and then compressed together for 10 to 45 seconds. The capsules were not sutured. If the adhesive properties were sufficient to maintain the severed surfaces of the spleen together and arrest bleeding after compression, the collagen passed the test. If the tissue surfaces would not adhere after compression for 45 seconds, the callagen failed the test. The results of these tests each on there different dogs, are reported in the column "In Vivo Tests A" of Table I. In these procedures, it was generally observed that although the fibrous mass was set with blood, the mass could be pressed with cotton or rayon without any apparent adhesion of the cotton or rayon fibers to the wet mass.

TABLE I

| Example | pH of Slurry in H$_2$O | Bulk Density #/cu. ft. | Surface Area sq.m. /gm. | HAT Rating | In Vivo A | B |
|---|---|---|---|---|---|---|
| I | 3.3 | 2.50 | 18.1–23.0 | 799 - AB+ 850 - A+ | Passed | I–II |
| II | 3.3 | 1.62 | 24.2 | 700 - A– | Passed | I |
| III | 3.0 | 3.06 | 3.9 | 700 - O+ | Passed | II |
| IV | 3.2 | 3.70 | 5.6 | (1) | (1) | I |
| V | 3.2 | 2.50 | 16.7 | 1025 - O+ | Passed | II |
| VI | 7.0 | 3.10 | 4.0 | 1100 - O+ | (1) | II |
| VII | 7.0 | 1.56 | 2.9 | 1220 - A+ | (1) | II |
| VIII | 9.0 | 2.80 | 1.5 | Failed* | (1) | II |
| IX | 9.0 | 2.75 | 1.4 | Failed* | (1) | III |
| X | 3.1 | 1.50 | 1.9 | 477 - A– 483 - AB+ | Passed | I |
| SURGICEL** | | | | Failed* | Poor | IV |
| OXYCEL** | | | | Failed* | Poor | IV |
| GELFOAM Sponge | | | | Failed* | Poor | IV |
| GELFOAM Powder | | | | Failed* | Failed | IV |

(1) Not tested
*All blood not absorbed
**Individual fibers pulled from fabrics

In another series of experiments on dogs, cuts were made in cutaneous, sub-cutaneous and muscle arteries an veins, the largest in the males being the external pudendals and in the females being the cranial superficial epigastrics; longitudinal incisions ¼" to ½" in depth and 1" in length were made in the spleen; and, wedge slices were made in the spleen by removal of a surface section ¼" to ½" in depth and ½" length on each side of the triangle. Each sample was used a minimum of four times by applying the sample to the bleedng site, applying pressure over the sample with a gauze sponge and observing the site each 30 seconds. The time was noted when the bleeding was controlled; that is, bleeding was arrested. The testing was "blind"; that is, the investigator was provided with the fluffy, fibrous product without knowledge of its history except in the case of the product of Example II.

Generally, an incision was made in the vessels or organs mentioned above and a gauze sponge applied to the bleeding site for 5 minutes to make certain that the blood itself did not coagulate and seal the wound within this period of time. The incision site was then mildly incised to reopen any vessel which had closed and to insure vigorous bleedng prior to the application of the fluffy fibrous product A sample of the product of Example II was then placed in the bleeding site as desribed above and the time noted when the bleeding had been arrested. After the bleeding has been arrested, the material was removed from the wound noting the tenaciousness with which it had adhered to the severed surfaces. The wound was then reopened to reinitiate free bleeding and one of the other samples of fluffy fibrous product used in the same manner. Again, the time for the sample to arrest bleeding and seal the wound wasted and the material removed. from the wound again noting the tenaciousness with which it adhered to the severed surfaces. Samles of the fluffy fibrous product of Example II were used at intervals between the other samples and at the end of the test samples.

The samples were given a rating by the investigator based upon four characteristics of the samples: (1) transfer properties which involved the transfer of the product to the wound and the adhesiveness of the product to forceps, rubber gloves and gauze sponges, (2) localization of the sample at the bleeding site, (3) the time for controlling or arresting the bleeding and (4) the adhesiveness to the severed surfaces. In preliminary testing of various samples, the investigator decided to use the product of Exmaple II as a standard or control because of its handling, hemostatic and adhesive properties and assigned a numerical Rating I to this sample for future testing. A Rating of II was given to samples which were satisfactory but were not quite as desirable as the standard or control samle. In some of these instances, it wasted that although bleeding had been controlled, there was a tendency toward a breakthrough bleeding which was arrested by applying additional pressure for 0.5 to 1.0 minute. Materials which performed about as well as or much like those given a Rating of II with respect to characteristics (2), (3) and (4) but had poor handling and transfer properties were given a Rating of III. A Rating of IV indicates that a product was defective in one or more of the characteristics, that is, it did not have proper transfer properties or did not arrest bleeding within 5 minutes or did not localize well around the wound or did not have sufficient adherence to the walls of the wound to seal the wound. In general, most products given this rating and considered unsatisfactory contained hornified fibers and gritty-like, hornified particles as reflected in high bulk densities.

The results of these experiments were as shown in the following table:

other foreign material on or embedded in the surfaces while in the hypochlorite solution. A convenient method involves drawing the corium sheet between two rotating cylindrical, stiff bristle brushes (stiff nylon bristles) under a copious stream of hydrogen free, distilled water whch may contain the hypochlorite.

Following scraping or brush washing, the corium sheets are rinsed with copious amounts of pydrogen free, distilled water and placed in hydrogen free, distilled water containing the sodium hypochlorite. The sheets are then cut into 3"-8" ×8" strips for convenience in subsequent processing and maintained in the hypochlorite solution until required for use. The strips are removed from the solution, placed in a centrifuge and pyrogen free, distilled water added. The strips are agitated in the water at slow speed for about ¼ hour and the exceess liquid separated by operating the centrifuge at high speed. The washing with the pyrogen free, distilled water is repeated until the effluent shows no detectable chlorine by the conventional silver choride test. The strips are then processed into the fluffy, fibrous product as described in Example X. All processing conducted in a conventional clean room.

In the processing of the corium into the partial salt of collagen, it is essential that in each step wherein the collagen or partial salt of collagen is treated in a liquid comprising ethanol, the mixture is agitated for a period sufficient to equalize the ethanol content of the liquid in the corium to that of the bulk liquid. Thus, each such treatment effects an increase in the ethanol content in the corium and prevents hornification upon final drying. Where the ethanol contains the ionizable acid, the treating step must be prolonged so as to effect the desired salt formation.

While the foregoing discussion has been directed to the use of fluffy, fibrous products, the fibrous products may be converted into non-woven webs or mats of desired thicknesses in accordance with conventional well known methods. In using a wet method such as commonly employed in forming appears and similar products, however, the fibrous collagen products are

TABLE II

| | Bleeding Controlled - Time in Minutes | | | | | |
|---|---|---|---|---|---|---|
| Example | Cutaneous Muscle | Pudendals | Epigastrics | Spleen Cut | Spleen Wedge | Rating |
| I | 2-2.5 | 5 | 3 | 1.5-2.0 | 1-1.5 | I - II |
| II | 2.4 ± 0.5 (6 Trials) | 2.0 ± 0.3 (20 Trials) | Not Tested | 1.8 ± 0.2 (19 Trials) | 1.7 ± 0.2 (13 Trials) | I |
| III | 1-3.5 | 1.5-4 | 3.5 | 1.0-1.5 | 2.5 | II |
| IV | 0.5 | 0.5-1.0 | Not Tested | 1.5 | 1.0 | I |
| V | 1.0 | 1.0 | Not Tested | 2.5 | 3.0 | II |
| VI | 1.0 | Not Tested | 3.0 | 1.0 | 1.0-1.5 | II |
| VII | 1.5 | Not Tested | 3.0 | Not Tested | 1.0 | II |
| VIII | 1.0 | 1.0 | Not Tested | 2.0 | 3.0 | II |
| IX | 3.0 | 3.0 | Not Tested | 3.0 | 3.5 | II |
| X | Not Tested | 2.0 | Not Tested | 2.5 | 3.0 | I |

In the production of the fluffy fibrous product to be utilized in human internal surgical procedures, it is necessary that processing be effected under conditions that eliminate pyrogenetic substances and microorganisms such as bacteria, yeasts, molds and the like. The raw material, such as green corium, is generally received in various sized sheets in frozen state. The frozen sheets are thawed by placing in hydrogen free, distilled water containing between 50 and 100 ppm, preferably 50-70 ppm, sodium hypochlorite, the solution having a pH between 7 and 9, preferably pH 7-8. The surfaces of the thawed sheets are scraped so as to loosen and/or remove substances such as dirt, loose protein and any slurried in a water-miscible organic liquid to form the furnish. The water-miscible organic liquid may be of the type used in producing the collagen products. Alternatively, the web may be formed by an air-laying method wherein the fibers are blown into a chamber and allowed to deposit in random arrangement on a formaminous collector such as a screen. In use, a thin web of the fibrous collagen product is cut, for example, to cover the spleen wedge as referred to hereinbefore, and pressed over the area in place of packing the fluffy, fibrous material over the area.

The products may be sterilized by subjecting them to the conventional ethylene oxide treatment. Alternatively, after packaging, the products may be sterilized by heating at a temperature of about 120° to 126° C. for 20 to 24 hours. If desired, antiseptics, bactericides, fungicides, germicides, medicinals and/or antibiotics may be mixed with the fibrous material. Where such additive is soluble in a water-miscible organic liquid as used in the production of the fluffy, fibrous product, the additive may be dissolved in the final wash bath whereby the additive becomes impregnated into the fibers.

The term "adhesion" as used this specification is used along with "adhesive" in the mechanical and chemical sense to designate what light be termed a cementing or gluing action and does not refer to the normal medical designation.

What is claimed is:

1. The method of preparing a mass of finely-divided fibrils and fibers having hemostatic properties and when placed on a wound combines with blood to form a mass that is self-adherent to the wound surfaces and seals the wound which comprises the steps of
    (a) placing water-wet collagen in an ethanol-water mixture, the amount of ethanol being sufficient to constitute from 90% to 50% by weight of the mixture including the water in the water-wet collagen,
    (b) agitating the mixture for a period sufficient to equalize the ethanol content of the collagen to that of the liquid,
    (c) separating the excess liquid fo the collagen,
    (d) placing the recovered collagen in an ethanol-ionizable acid mixture, the amount of acid being sufficient to form a partial salt of collagen containing from about 50% to 90% of the theoretical stoichiometric bound acid content,
    (e) agitating the mixture for from about 3 to about 20 hours to equalize the ethanol content of the collagen to that of the liquid and to effect the reaction of the collagen with the acid to form a partial salt of collagen,
    (f) separating the excess liquid from the partial salt,
    (g) subjecting the recovered partial salt to treatment with ethanol and separating the partial salt from the liquid a sufficient number of cycles until the water content of the partial salt has been reduced to 1%,
    (h) vacuum drying the recovered partial salt to a volatiles content of about 1%,
    (i) conditioning the dried partial salt to a volatiles content of about 8% to 15%, and
    (j) subjecting the conditioned partial salt to a fiberizing and deaggregation or fluffing operation to form a mass of finely-divded fibrils and fibers, the mass of fibrils and fibers consisting of fibrils and fibers at least about 5% by weight of which have an effective length of not more than 1 mm. and not more than about 10% by weight of which have an effective length above 12 mm., the mass of fibrils and fibers having a surface area of at least 1 square meter per gram, having a bulk density of not more tha 8 pounds per cubic foot and exhibiting a HAT test of not more than 1500 when wet with blood.

2. The method as defined in claim 1 wherein the collagen is corium in the form of water-wet chips before treatment with an ethanol-water mixture containing about 75% ethanol and about 25% water by weight.

3. The method as defined in claim 1 wherein the collagen is corium and the corium is fiberized before treatment with an ethanol-water mixture containing about 75% ethanol and about 25% water by weight.

4. The method as defined in claim 1 wherein the collagen is corium and the ionizable acid is hydrochloric acid.

* * * * *

UNITED STATES PATENT AND TRADEMARK OFFICE
CERTIFICATE OF CORRECTION

PATENT NO. : 4,148,664
DATED : April 10, 1979
INVENTOR(S) : Mamerto M. Cruz, Jr.

It is certified that error appears in the above–identified patent and that said Letters Patent are hereby corrected as shown below:

Abstract, line 7, "a" should read --an--. Column 4, line 68, "used the" should read --used in the --. Column 5, line 17, "35" should read -- ± --; line 52 "the blood" should read --by the blood--. Column 6, line 4 "an" should read --and--; line 12 "above mm." should read --above 12 mm.--; line 27 "an" should read --any--; line 45 "referred" should read --preferred--; line 58 "flow" should read --follow--. Column 7, line 12 "MIll" should read --Mill--. Column 9, line 8 "callagen" should read --collagen--; line 41 "pergram" should read --per gram--; line 45 "blood" should read --blood.--; line 48 "act" should read --action--; line 65 "makng" should read --making--. Column 10, line 7 "callagen" should read --collagen--; line 8 "there" should read --three--; line 11 "set" should read --wet--; line 40 "an" should read --and--; line 62 "product" should read --product.--; line 65 "has" should read --had--. Column 11, line 3 "wasted" should read --was noted--; line 4 "removed." should read --removed--; line 6 "Samles" should read --Samples--; line 18 "Exmaple" should read --Example--; line 23 "Samle." should read --sample.-- ; line 24 "wasted" should read --was noted--; line 63 "hydrogen" should read --pyrogen--. Column 12, line 5 "hydrogen" should read --pyrogen--; line 6 "whch" should read --which--; line 8 "pydrogen" should read --pyrogen--; line 9 "hydrogen" should read --pyrogen--; line 11 "3"-8"x8"" should read --3"-4"x8"--; line 20 "choride" should read --chloride--; line 40 "appears" should read --papers--. Column 13, line 12 "used this" should read --used in this--; line 30, "fo" should read --from--.

UNITED STATES PATENT AND TRADEMARK OFFICE
CERTIFICATE OF CORRECTION

PATENT NO. : 4,148,664
DATED : April 10, 1979
INVENTOR(S) : Mamerto M. Cruz, Jr.

It is certified that error appears in the above–identified patent and that said Letters Patent are hereby corrected as shown below:

Column 14, line 16, "finely-divded" should read -- finely-divided --; line 23, "tha" should read -- than --.

Signed and Sealed this

Eighteenth Day of September 1979

[SEAL]

Attest:

LUTRELLE F. PARKER

Attesting Officer     Acting Commissioner of Patents and Trademarks